United States Patent
Jahagirdar et al.

(10) Patent No.: US 8,383,151 B2
(45) Date of Patent: Feb. 26, 2013

(54) PHARMACEUTICAL COMPOSITIONS OF RIFAXIMIN

(75) Inventors: Harshal Anil Jahagirdar, Pune (IN); Rajesh Kulkarni, Pune (IN); Shirishkumar Kulkarni, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 410 days.

(21) Appl. No.: 12/144,453

(22) Filed: Jun. 23, 2008

(65) Prior Publication Data

US 2009/0028940 A1    Jan. 29, 2009

(30) Foreign Application Priority Data

Jul. 6, 2007  (IN) .............................. 968/KOL/2007

(51) Int. Cl.
*A61K 9/20* (2006.01)
(52) U.S. Cl. ........ 424/464; 424/468; 514/279; 514/394; 514/964
(58) Field of Classification Search .................. None
See application file for complete search history.

(56) References Cited

U.S. PATENT DOCUMENTS 4,341,785 A   7/1982   Marchi et al.
2010/0016333 A1*  1/2010  Flanner et al. ........... 514/254.11

FOREIGN PATENT DOCUMENTS

IT           1154655       1/1987
WO    WO 2006/094737   *  9/2006

* cited by examiner

*Primary Examiner* — Robert A Wax
*Assistant Examiner* — Hasan Ahmed
(74) *Attorney, Agent, or Firm* — Merchant & Gould P.C.

(57) ABSTRACT

A pharmaceutical composition comprising therapeutically effective amount of rifaximin or pharmaceutically acceptable salt or enantiomer or polymorph thereof, pharmaceutically acceptable excipient(s) and release controlling agent(s). Pharmaceutical composition of rifaximin comprising: at least two entities wherein one entity is an immediate release or fast release and the other is controlled release. The pharmaceutical composition in the form of multilayer tablet comprising, at least one layer comprising, therapeutically effective amount of rifaximin or pharmaceutically acceptable salt or enantiomer or polymorph thereof, pharmaceutically acceptable excipient(s); said layer providing controlled release rifaximin; and at least one layer which provides increased residence time of the dosage form in the gastrointestinal tract. The pharmaceutical formulation comprising rifaximin having an in vitro dissolution profile, wherein about 70% of rifaximin is released in about 24 hours. The composition comprising therapeutically effective amount of rifaximin or pharmaceutically acceptable salt(s) or enantiomer(s) or polymorph(s) thereof, one or more release controlling agent(s) and pharmaceutically acceptable excipient(s) causing pathogenic eradication.

39 Claims, 1 Drawing Sheet

PHARMACEUTICAL COMPOSITIONS OF RIFAXIMIN

FIELD OF THE INVENTION

This invention relates to pharmaceutical compositions of rifaximin for controlling the release and/or increasing the residence time in the gastrointestinal tract and the process of preparing them.

BACKGROUND OF THE INVENTION

The antibiotic rifaximin was originally disclosed in Italy as IT Patent 1154655. The related U.S. Pat. No. 4,341,785 to Marchi et al. discloses imidazo-rifamycin derivatives having antibacterial utility, and the related process for preparing it. The US '785 patent also discloses a pharmaceutical antibacterial composition and a method of using it to treat antibacterial diseases of the gastrointestinal tract (GIT).

Rifaximin is essentially a non-absorbable, non-systemic, semi-synthetic antibiotic, related to rifamycin. The antimicrobial spectrum (in vitro) includes most gram-positive and gram-negative bacteria; and both aerobes and anaerobes. Rifaximin is approved in certain countries for the treatment of pathologies whose etiology is in part or totally due to intestinal acute and chronic infections sustained by Gram-positive and Gram-negative bacteria, with diarrhea syndromes, altered intestinal microbial flora, summer diarrhea-like episodes, traveler's diarrhea and enterocolitis; pre- and post-surgery prophylaxis of the infective complications in gastro intestinal surgery; and hyperammonaemia therapy as coadjutant. The drug has been found to have no significant side effects.

Rifaximin is currently marketed as tablets at the dosage of 200 mg for traveler's diarrhea under the brand name "Xifaxan®".

Oral drug administration is by far the most preferable route for taking medications. However, on oral administration, normal or pathological stomach voiding and intestinal peristaltic movements limit the time for which a drug-releasing dosage form remains in the gastrointestinal tract or at the required site of action. As the drug is locally acting it should remain at the site of action/in the GIT for the sufficient period of time. Specifically, during pathological conditions such as diarrhea, peristaltic movement of the GI Tract is increased. Therefore, GI transit time of dosage forms is lesser than normal. Hence conventional dosage forms have shorter residence time at the required site of action and need to be dosed frequently in order to be therapeutically effective. A rational approach to solve this problem and to improve pharmacodynamic profiles is to retain the drug reservoir at the site of action, and to release the drug in a controlled manner, for a prolonged period of time. We have now developed a controlled release and/or mucoadhesive dosage form of rifaximin, which surprisingly extends the GI residence time of rifaximin.

OBJECTS OF THE INVENTION

The object of the present invention is to provide a pharmaceutical composition comprising a therapeutically effective amount of rifaximin or a pharmaceutically acceptable salt(s) or enantiomer(s) or polymorph(s) thereof, one or more release controlling agent(s) and pharmaceutically acceptable excipient(s).

Another object of the present invention is to provide a pharmaceutical composition comprising a therapeutically effective amount of rifaximin or a pharmaceutically acceptable salt(s) or enantiomer(s) or polymorph(s) thereof, one or more release controlling agent(s) and pharmaceutically acceptable excipient(s), wherein the composition is formulated to increase the residence time of rifaximin in the gastrointestinal tract.

Another object of the invention is to provide a pharmaceutical composition comprising rifaximin used to increase patient compliance for treatment of traveler's diarrhea, hepatic encephalopathy, infectious diarrhea, diverticular disease, an antibacterial prophylactic prior to colon surgery, irritable bowel syndrome, Crohn's disease, *Clostridum difficile*-associated diarrhea, small intestinal bacterial overgrowth, traveler's diarrhea prophylaxis, dysentery, pouchitis, peptic ulcer disease, surgical prophylaxis and gastric dyspepsia. Another object of the invention is to provide a pharmaceutical composition comprising rifaximin used to increase patient compliance for treatment of traveler's diarrhea.

Yet another object of the invention is to provide a method of treating *klebsiella* induced traveler's diarrhea comprising administering a once daily pharmaceutical composition comprising therapeutically effective amount of rifaximin or pharmaceutically acceptable salt(s) or enantiomer(s) or polymorph(s) thereof, one or more release controlling agent(s) and pharmaceutically acceptable excipient(s).

Another object of the present invention is to provide a pharmaceutical composition of rifaximin comprising: at least two entities wherein one entity is an immediate release or fast release and the other is controlled release.

Another object of the present invention is to provide a pharmaceutical composition of rifaximin comprising: at least two entities wherein one entity is controlled release and the other is a bioadhesive.

Another object of the invention is to produce a pharmaceutical composition in the form of a multilayer tablet comprising, a) at least one layer which comprises, a therapeutically effective amount of rifaximin or a pharmaceutically acceptable salt(s) or enantiomer(s) or polymorph(s) thereof, pharmaceutically acceptable excipient(s); wherein the said layer provides a controlled release rifaximin; and b) at least another layer which provides increased residence time of the dosage form in the gastrointestinal tract.

Yet another object of the present invention is to provide a pharmaceutical formulation comprising rifaximin having an in vitro dissolution profile, when measured in a type II Paddle dissolution apparatus, in 6.8 phosphate buffer with 1.5% sodium lauryl sulphate (SLS) at about 100 rpm, wherein about 70% of rifaximin is released in about 24 hours.

Another object of the invention is to provide a once daily pharmaceutical composition comprising rifaximin having an in vitro dissolution profile, when measured in a type II Paddle dissolution apparatus, in 6.8 phosphate buffer with 1.5% SLS at about 100 rpm, wherein about 20% to about 50% of the drug is released in about 8 hrs, about 30% to about 70% of drug is released in about 12 hrs and about more than 70% of drug is released in about 24 hrs.

Yet another object of the invention is to provide a pharmaceutical composition comprising a therapeutically effective amount of rifaximin or a pharmaceutically acceptable salt(s) or enantiomer(s) or polymorph(s) thereof, one or more release controlling agent(s) and pharmaceutically acceptable excipient(s), wherein the composition is formulated to increase the residence time of rifaximin in the gastrointestinal tract having an adhesive strength, measured as a force of detachment, of at least 100 mN when measured using advanced force gauge equipment (manufactured by Mecmesin, West Sussex, England).

Another object of the invention is to provide a once daily pharmaceutical composition comprising therapeutically effective amount of rifaximin or pharmaceutically acceptable salt(s) or enantiomer(s) or polymorph(s) thereof, one or more release controlling agent(s) and pharmaceutically acceptable excipient(s) which results in eradication of at least 70% of pathogens.

Another object of the invention is to provide a once daily pharmaceutical composition comprising therapeutically effective amount of rifaximin or pharmaceutically acceptable salt(s) or enantiomer(s) or polymorph(s) thereof, one or more release controlling agent(s) and pharmaceutically acceptable excipient(s) resulting in time for last unformed stools for $E.\ coli$ positive population in the range of about 8 to about 90 hrs.

Another object of the invention is to provide a once daily pharmaceutical composition comprising therapeutically effective amount of rifaximin or pharmaceutically acceptable salt(s) or enantiomer(s) or polymorph(s) thereof, one or more release controlling agent(s) and pharmaceutically acceptable excipient(s) resulting in time for last unformed stools for $E.\ coli$ positive population in the range of about 20 to about 90 hrs.

DETAILED DESCRIPTION OF THE INVENTION

The present invention is directed towards a pharmaceutical composition comprising a therapeutically effective amount of rifaximin or a pharmaceutically acceptable salt(s) or enantiomer(s) or polymorph(s) thereof, one or more release controlling agent(s) and pharmaceutically acceptable excipient(s).

The present invention is further directed towards a pharmaceutical composition comprising a therapeutically effective amount of rifaximin or a pharmaceutically acceptable salt(s) or enantiomer(s) or polymorph(s) thereof, one or more release controlling agent(s) and pharmaceutically acceptable excipient(s) wherein the composition is formulated to increase the residence time of rifaximin in the gastrointestinal tract.

"Therapeutically effective amount" means that the amount of active agent, which halts or reduces the progress of the condition being treated or which otherwise completely or partly cures or acts palliatively on the condition. A person skilled in the art can easily determine such an amount by routine experimentation and with an undue burden.

"Controlled release," means drug delivery system releasing the drug at a predetermined rate, locally or systemically, for a specified period of time. Controlled release can be used interchangeably with prolonged release, programmed release, timed release, extended release, sustained release and other such dosage forms.

"Optional" or "optionally" means that the subsequently described circumstance may or may not occur, so that the description includes instances where the circumstance occurs and instances where it does not.

By "pharmaceutically acceptable" is meant a carrier comprised of a material that is not biologically or otherwise undesirable.

"Entities" or "Entity" can be interchangeably used with granules, pellets, beads, minitablets and the like.

"Bioadhesion" is defined as the ability of a material to adhere to a biological tissue for an extended period of time. Bioadhesion is one solution to the problem of inadequate residence time resulting from stomach emptying and intestinal peristalsis, and from displacement by ciliary movement. Bioadhesive properties of polymers are affected by both the nature of the polymer and by the nature of the surrounding media.

Bioadhesive and mucoadhesive can be used interchangeably.

"Increased residence time" for purpose of this invention, residence time is the time required for a pharmaceutical dosage form to transit through the stomach to the rectum i.e. the pharmaceutical dosage forms of the invention may have an increased retention time in the stomach and/or small and/or large intestine, or in the area of the gastrointestinal tract that is site of action or absorption of the drug contained in the pharmaceutical dosage form. For example, pharmaceutical dosage forms of the invention can be retained in the small intestine (or one or two portions thereof, selected from the duodenum, the jejunum and the ileum). These pharmaceutical dosage forms as a whole, may include a controlled release or bioadhesive coating that is applied to at least one surface of the dosage form.

In a preferred embodiment of the present invention the increase in residence time of rifaximin formulation in the gastrointestinal tract is achieved by bioadhesion wherein bioadhesion is achieved using polymers having affinity for gastrointestinal mucosa. Examples of mucoadhesives for use in the embodiments disclosed herein include, but are not limited to, natural, semisynthetic and synthetic polymers.

Natural polymers include but are not limited to proteins (e.g., hydrophilic proteins), such as pectin, zein, modified zein, casein, gelatin, gluten, serum albumin, or collagen, chitosan, oligosaccharides and polysaccharides such as cellulose, dextrans, tamarind seed polysaccharide, gellan, carrageenan, xanthan gum, gum Arabic; hyaluronic acid, polyhyaluronic acid, alginic acid, sodium alginate.

When the bioadhesive polymer is a synthetic polymer, the synthetic polymer is typically selected from but are not limited to polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, polystyrene, polymers of acrylic and methacrylic esters, polylactides, poly(butyric acid), poly (valeric acid), poly(lactide-co-glycolide), polyanhydrides, polyorthoesters, poly(fumaric acid), poly(maleic acid), and blends and copolymers or mixtures thereof.

Other polymers suitable for use in the invention include, but are not limited to, methyl cellulose, ethyl cellulose, hydroxypropyl cellulose, hydroxypropylmethyl cellulose, hydroxybutylmethyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly (ethyl methacrylate), poly (butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), polyvinyl acetate), polyvinyl chloride, polystyrene, polyvinyl pyrrolidone, and polyvinylphenol. Polylactides, polyglycolides and copolymers thereof, poly(ethylene terephthalate), poly(butyric acid), poly(valeric acid), poly(lactide-co-caprolactone), poly[lactide-co-glycolide], polyanhydrides (e.g., poly(adipic anhydride)), polyorthoesters, blends and copolymers thereof.

Another group of polymers suitable for use as bioadhesive polymers but not necessarily limited to polymers having a hydrophobic backbone with at least one hydrophobic group pendant from the backbone. Suitable hydrophobic groups are groups that are generally non-polar. Examples of such hydrophobic groups include alkyl, alkenyl and alkynyl groups. Preferably, the hydrophobic groups are selected to not interfere and instead to enhance the bioadhesiveness of the polymers.

A further group of polymers suitable for use as bioadhesive polymers but not necessarily limited to polymers having a hydrophobic backbone with at least one hydrophilic group pendant from the backbone. Suitable hydrophilic groups include groups that are capable of hydrogen bonding or electrostatically bonding to another functional group. Example of such hydrophilic groups include negatively charged groups such as carboxylic acids, sulfonic acids and phosphonic acids, positively charged groups such as (protonated) amines and neutral, polar groups such as amides and imines.

Preferably, the hydrophilic groups are selected not to interfere and instead to enhance the bioadhesiveness of the polymers. In embodiments of the present invention, a pharmaceutical composition comprises an active agent and at least one swellable polymer.

Swellable polymers include, but are not limited to, a crosslinked poly(acrylic acid), a poly(alkylene oxide), a poly-vinyl alcohol), a polyvinyl pyrrolidone); a polyurethane hydrogel, a maleic anhydride polymer, such as a maleic anhydride copolymer, a cellulose polymer, a polysaccharide, starch, and starch based polymers.

Polymers can be modified by increasing the number of carboxylic groups accessible during biodegradation, or on the polymer surface. The polymers can also be modified by binding amino groups to the polymer. The polymers can be modified using any of a number of different coupling chemistries available in the art to covalently attach ligand molecules with bioadhesive properties to the surface-exposed molecules of the polymeric microspheres.

Lectins can be covalently attached to polymers to render them target specific to the mucin and mucosal cell layer. The attachment of any positively charged ligand, such as polyethyleneimine or polylysine, to a polymer may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most polymers with the appropriate chemistry, such as with carbodiimidazole (CDI), and be expected to influence the binding to the gut. For example, polyclonal antibodies raised against components of mucin or else intact mucin, when covalently coupled to a polymer, would provide for increased bioadhesion. Similarly, antibodies directed against specific cell surface receptors exposed on the lumenal surface of the intestinal tract would increase the residence time when coupled to polymers using the appropriate chemistry. The ligand affinity need not be based only on electrostatic charge, but other useful physical parameters such as solubility in mucin or specific affinity to carbohydrate groups.

The covalent attachment of any of the natural components of mucin in either pure or partially purified form to the polymers generally increases the solubility of the polymer in the mucin layer. The list of useful ligands include but are not limited to the following: sialic acid, neuraminic acid, n-acetyl-neuraminic acid, n-glycolylneuraminic acid, 4-acetyl-n-acetylneuraminic acid, diacetyl-n-acetyl-neuraminic acid, glucuronic acid, iduronic acid, galactose, glucose, mannose, fructose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, such as polyaspartic acid and polyglutamic acid, may also increase bioadhesiveness. The polyamino chains would increase bioadhesion by means of chain entanglement in mucin strands as well as by increased carboxylic charge.

In another embodiment the formulation of the present invention further comprises solubilizing agents defined as the agents that help the drug to solubilize either in formulation or in the site of absorption or action. Solubilizing agents include but are not limited to surfactants, cyclodextrin and its derivatives, lipophilic substances or any combination thereof.

Unlimiting examples of surfactants include water-soluble or water dispersible nonionic, semi-polar nonionic, anionic, cationic, amphoteric, or zwitterionic surface-active agents; or any combination thereof.

Other solubilizing agents include but not necessarily limited to vitamin E substance and its derivatives; monohydric alcohol esters such as trialkyl citrates, lactones and lower alcohol fatty acid esters; nitrogen-containing solvents; phospholipids; glycerol acetates such as acetin, diacetin and triacetin; glycerol fatty acid esters such as mono-, di- and triglycerides and acetylated mono- and diglycerides; propylene glycol esters; ethylene glycol esters; and combinations thereof.

Pharmaceutically acceptable excipients include but are not limited to binders, diluents, lubricants, glidants and surface-active agents.

The amount of additive employed will depend upon how much active agent is to be used. One excipient can perform more than one function.

Binders include, but are not limited to, starches such as potato starch, wheat starch, corn starch; microcrystalline cellulose such as products known under the registered trade marks Avicel, Filtrak, Heweten or Pharmacel; celluloses such as hydroxypropyl cellulose, hydroxyethyl cellulose, hydroxypropylmethyl cellulose (HPMC), ethyl cellulose, sodium carboxy methyl cellulose; natural gums like acacia, alginic acid, guar gum; liquid glucose, dextrin, povidone, syrup, polyethylene oxide, polyvinyl pyrrolidone, poly-N-vinyl amide, polyethylene glycol, gelatin, poly propylene glycol, tragacanth, combinations thereof and other materials known to one of ordinary skill in the art and mixtures thereof.

Fillers or diluents, which include, but are not limited to confectioner's sugar, compressible sugar, dextrates, dextrin, dextrose, fructose, lactitol, mannitol, sucrose, starch, lactose, xylitol, sorbitol, talc, microcrystalline cellulose, calcium carbonate, calcium phosphate dibasic or tribasic, calcium sulphate, and the like can be used.

Lubricants may be selected from, but are not limited to, those conventionally known in the art such as Mg, Al or Ca or Zn stearate, polyethylene glycol, glyceryl behenate, mineral oil, sodium stearyl fumarate, stearic acid, hydrogenated vegetable oil and talc.

Glidants include, but are not limited to, silicon dioxide; magnesium trisilicate, powdered cellulose, starch, talc and tribasic calcium phosphate, calcium silicate, magnesium silicate, colloidal silicon dioxide, silicon hydrogel and other materials known to one of ordinary skill in the art.

The present formulations may optionally contain a surface-active agent. The preferred agent is copolymers composed of a central hydrophobic chain of polyoxypropylene (poly (propylene oxide)) and polyoxyethylene (poly(ethylene oxide)) that is well known as poloxamer. However, other agents may also be employed such as dioctyl sodium sulfosuccinate (DSS), triethanolamine, sodium lauryl sulphate (SLS), polyoxyethylene sorbitan and poloxalkol derivatives, quaternary ammonium salts or other pharmaceutically acceptable surface-active agents known to one ordinary skilled in the art.

The pharmaceutical formulation according to the present invention include but is not limited to tablets (single layered tablets, multilayered tablets, mini tablets, bioadhesive tablets, caplets, matrix tablets, tablet within a tablet, mucoadhesive tablets, modified release tablets, pulsatile release tablets, timed release tablets), pellets, beads, granules, sustained release formulations, capsules, microcapsules, tablets in capsules and microspheres, matrix formulations, microencapsulation and powder/pellets/granules for suspension.

The pharmaceutical dosage form of the invention can optionally have one or more coatings such as film coating, sugar coating, enteric coating, bioadhesive coating and other coatings known in the art. These coatings help pharmaceutical formulations to release the drug at the required site of action. In one example, the additional coating prevents the dosage from contacting the mouth or esophagus. In another example, the additional coating remains intact until reaching the small intestine (e.g., an enteric coating). Premature exposure of a bioadhesive layer or dissolution of a pharmaceutical dosage form in the mouth can be prevented with a layer or coating of hydrophilic polymers such as HPMC or gelatin. Optionally, Eudragit FS 30D or other suitable polymer may be incorporated in coating composition to retard the release of the drug to ensure drug release in the colon.

These coating layers comprises one or more excipients selected from the group comprising coating agents, opacifiers, taste-masking agents, fillers, polishing agents, colouring agents, antitacking agents and the like.

Coating agents which are useful in the coating process, include, but are not limited to, polysaccharides such as maltodextrin, alkyl celluloses such as methyl or ethyl cellulose, hydroxyalkylcelluloses (e.g. hydroxypropylcellulose or hydroxypropylmethylcelluloses); polyvinylpyrrolidone, acacia, corn, sucrose, gelatin, shellac, cellulose acetate pthalate, lipids, synthetic resins, acrylic polymers, opadry, polyvinyl alcohol (PVA), copolymers of vinylpyrrolidone and vinyl acetate (e.g. marketed under the brand name of Plasdone) and polymers based on methacrylic acid such as those marketed under the brand name of Eudragit. These may be applied from aqueous or non-aqueous systems or combinations of aqueous and non-aqueous systems as appropriate. Additives can be included along with the film formers to obtain satisfactory films. These additives can include plasticizers such as dibutyl phthalate, triethyl citrate, polyethylene glycol (PEG) and the like, antitacking agents such as talc, stearic acid, magnesium stearate and colloidal silicon dioxide and the like, surfactants such as polysorbates and sodium lauryl sulphate, fillers such as talc, precipitated calcium carbonate, Polishing agents such as Beeswax, carnauba wax, synthetic chlorinated wax and opacifying agents such as titanium dioxide and the like. All these excipients can be used at levels well known to the persons skilled in the art.

Pharmaceutical dosage forms of the invention can be coated by a wide variety of methods. Suitable methods include compression coating, coating in a fluidized bed or a pan and hot melt (extrusion) coating. Such methods are well known to those skilled in the art.

Non-permeable coatings of insoluble polymers, e.g., cellulose acetate, ethylcellulose, can be used as enteric coatings for delayed/modified release (DR/MR) by inclusion of soluble pore formers in the coating, e.g., PEG, PVA, sugars, salts, detergents, triethyl citrate, triacetin, etc.

Also, coatings of polymers that are susceptible to enzymatic cleavage by colonic bacteria are another means of ensuring release to distal ileum and ascending colon. Materials such as calcium pectinate can be applied as coatings to dosage form and multiparticulates and disintegrate in the lower gastrointestinal tract, due to bacterial action. Calcium pectinate capsules for encapsulation of bioadhesive multiparticulates are also available.

In an embodiment the coating further comprises the drug.

In a preferred embodiment of the present invention the pharmaceutical formulation is multilayer tablets comprising a first, a second and/or a third layer, where each layer includes one or more excipient(s).

Multi-layer or gradient tablets can be assembled in several different ways.

In one embodiment, the tablet comprises at least one solid core and two outer layers, each comprising one or more pharmaceutical polymers and/or pharmaceutical excipients. The core comprises active ingredient and rate-controlling polymer. The two outer layers are bioadhesive.

In another embodiment, the tablet comprises at least one core and two outer layers, each comprising drug and one or more pharmaceutical polymers and/or pharmaceutical excipients. Such tablets can also be used to commence release of different drugs at different times, by inclusion of different drugs in separate layers.

In another embodiment, the multi-layer tablet comprises of a core and two outer layers, each comprising a drug and one or more pharmaceutical polymers or pharmaceutical excipients, wherein at least one polymer or excipient is hydrophobic.

In another preferred embodiment the present invention relates to formulation which comprises multilayer tablet wherein at least one layer consist of a release controlling polymer and the active ingredient and at least one layer which consist of bioadhesive polymer, where each layer includes one or more excipients.

In another embodiment the present invention relates to formulation which comprises multilayer tablet wherein at least one layer consist of a release controlling polymer and at least one layer which consist of bioadhesive polymer, where each layer includes one or more excipients and drug.

The release controlling polymers can be hydrophilic, hydrophobic or combination thereof.

The hydrophilic rate-controlling polymer includes but are not limited to hydroxyethylcellulose, hydroxypropyl cellulose, Hydroxypropyl Methylcellulose, sodium carboxymethyl cellulose, sodium alginate, carbomer (Carbopol™), xanthan gum, guar gum, locust bean gum, poly vinyl acetate, polyvinyl alcohol. Preferably the rate-controlling polymer is hydroxypropylmethylcellulose (Low viscosity grade).

The hydrophobic rate controlling agent in matrix includes but are not limited to hydrogenated vegetable oil, but other suitable agents include purified grades of beeswax; fatty acids; long chain fatty alcohols, such as cetyl alcohol, myristyl alcohol, and stearyl alcohol; glycerides such as glyceryl esters of fatty acids like glyceryl monostearate, glyceryl distearate, glyceryl esters of hydrogenated castor oil and the like; oils such as mineral oil and the like, or acetylated glycerides;

ethyl cellulose, stearic acid, paraffin, carnauba wax, talc; and the stearate salts such as calcium, magnesium, zinc and other materials known to one of ordinary skill in the art.

In embodiments of the present invention, a pharmaceutical composition comprises an active agent and at least one swellable polymer. Swellable polymers include, but are not limited to, a crosslinked poly(acrylic acid), a poly(alkylene oxide), a polyvinyl alcohol), a polyvinyl pyrrolidone); a polyurethane hydrogel, a maleic anhydride polymer, such as a maleic anhydride copolymer, a cellulose polymer, a polysaccharide, starch, and starch based polymers.

In another embodiment of the present invention the pharmaceutical composition of rifaximin comprises: at least two entities wherein one entity is an immediate release or fast release and the other is controlled release.

In another embodiment of the present invention the pharmaceutical composition of rifaximin comprises: at least two entities wherein one entity is an immediate release or fast release and the other is a bioadhesive.

In another embodiment of the present invention the pharmaceutical composition of rifaximin comprises: at least two entities wherein one entity is controlled release and the other is a bioadhesive.

The pharmaceutical composition of the invention can be formed by various methods known in the art such as by dry granulation, wet granulation, melt granulation, direct compression, double compression, extrusion spheronization, layering and the like.

In a preferred embodiment, the process of making the pharmaceutical formulation of the invention comprises as described below:

vi) blending the active agent and pharmaceutically acceptable additives,
vii) Subjecting the blend to slugging/compaction to form a coprimate
viii) Converting the coprimate to granules and
ix) Compressing the granules to form the solid oral dosage form.
x) The compressed granules are optionally coated.

Compaction of the blend into coprimate may be carried out using a slugging technique or roller compaction. The milling of the granules may be carried out according to conventional milling methods.

The process of wet granulation includes aqueous or non-aqueous granulation. The wet granulation process comprises the admixing of the active ingredient with diluent(s) and/or rate controlling polymer, and granulation of the blend with the binder mass to form the wet mass followed by drying and sizing. The binder may optionally be admixed with the dry blend and granulation performed with aqueous or non-aqueous solvent. The solvent for the non-aqueous granulation is selected from ethanol, isopropyl alcohol and dichloromethane.

Rifaximin is approved for the treatment of travelers' diarrhea in adults and in children 12-years of age and older. Rifaximin has also been evaluated for the treatment of hepatic encephalopathy, infectious diarrhea, and diverticular disease and as an antibacterial prophylactic prior to colon surgery, gastric dyspepsia caused by bacteria known as *Helicobacter pylori*.

In an aspect of the present invention includes a method of increasing patient compliance for treatment of traveler's diarrhea, hepatic encephalopathy, infectious diarrhea, diverticular disease, an antibacterial prophylactic prior to colon surgery, irritable bowel syndrome, Crohn's disease, *Clostridum difficile*-associated diarrhea, small intestinal bacterial overgrowth, traveler's diarrhea prophylaxis, dysentery, pouchitis, peptic ulcer disease, surgical prophylaxis and gastric dyspepsia by administering once daily dosage form comprising rifaximin.

The pharmaceutical composition of the present invention contain, for example, from about 0.1% to 90% of rifaximin. Presently for the approved indication of travelers' diarrhea, rifaximin is administered 200 milligrams orally 3 times a day as immediate release dosage form for 3 days in adults and in children 12-years of age and older. The therapeutic dose varies according to the body weight and the acuteness of the pathology; a daily dose between 20 mg and 2400 mg, preferably 200 mg to 2000 mg, administered in a single dose or divided into 2 or 3 doses.

In an embodiment of the present invention in order to improve the patient compliance and target the formulation in intestine, a bioadhesive, controlled release once daily (600 mg) of rifaximin is explored.

The foregoing examples are illustrative embodiments of the invention and are merely exemplary. A person skilled in the art may make variations and modifications without deviating from the spirit and scope of the invention. All such modifications and variations are intended to be included within the scope of the invention.

EXAMPLES

Example 1

A First Layer

| Ingredients | % w/w |
|---|---|
| Rifaximin | 30 |
| Hydroxypropylmethyl cellulose) HPMC | 10 |
| Poloxamer | 10 |
| Diluents (e.g., Mannitol or DCP or MCC) | 40 |
| Colloidal silicon dioxide | 5 |
| Magnesium stearate | 5 |

Procedure:
i) Sift Rifaximin, diluent, HPMC and Poloxamer through suitable sieve.
ii) Dry blend (i) in a blender.
iii) Sift colloidal silicon dioxide and magnesium stearate through suitable sieve.
iv) Lubricate (ii) with (iii) in a blender.

B) Second Layer

| Ingredients | % w/w |
|---|---|
| HPMC | 50 |
| Polyethylene Oxide (PEO) | 35 |
| Colloidal silicon dioxide | 10 |
| Magnesium stearate | 5 | i) Sift HPMC and PEO through suitable sieve
ii) Dry blend (i) in a blender.
iii) Sift colloidal silicon dioxide and magnesium stearate through suitable sieve.
iv) Lubricate (ii) with (iii) in a blender.

Blends of A and B are then compressed into bilayer tablets or tablet in tablet or individually compressed into mini-tablets and filled into capsules.

The uncoated tablet then film coated 2-3% weight gain with following composition.

| Ingredients | % w/w |
|---|---|
| Hypromellose | 67 |
| Lactose monohydrate | 17 |
| Polyethylene glycol | 3 |
| Talc | 4 |
| Titanium dioxide | 3 |
| Iron Oxide Red | 3 |
| Yellow Iron Oxide | 3 |
| Water | Q.S. |

Example 2

A) First Layer

| Ingredients | % w/w |
|---|---|
| Rifaximin | 40 |
| Diluents (e.g., Mannitol or DCP or MCC) | 15 |
| HPMC | 15 |
| PEO | 20 |
| Colloidal silicon dioxide | 7 |
| Magnesium stearate | 3 |
| Water | QS |

Procedure:
i) Sift Rifaximin, diluent and PEO through specific sieve and mix in a blender.
ii) Add HPMC to water under stirring.
iii) Granulate (i) with (ii) and dry the wet mass in a fluid bed dryer.
iv) Granules of (iii) passed through suitable sieve.
v) Sift colloidal silicon dioxide and magnesium stearate through suitable sieve.
vi) Lubricate (iv) with (v).

B) Second Layer

| Ingredients | % w/w |
|---|---|
| HPMC | 50 |
| PEO | 35 |
| Colloidal silicon dioxide | 10 |
| Magnesium stearate | 5 | i) Sift HPMC and PEO through suitable sieve
ii) Dry blend (i) in a blender.
iii) Sift colloidal silicon dioxide and magnesium stearate through suitable sieve.
iv) Lubricate (ii) with (iii) in a blender.

Compress both A and B to form bilayer tablet or individually compressed into mini-tablets and filled into capsules.

The uncoated tablet then Enteric coated with 5-10% weight gain with following composition.

| Composition | % w/w |
|---|---|
| Eudragit L 100 | 40 |
| Eudragit S 100 | 40 |
| TEC | 8 |
| Talc | 12 |
| IPA | QS |
| Water | QS |

Example 3

A) First Layer

| Ingredients | % w/w |
|---|---|
| Rifaximin | 50 |
| Diluents (e.g., Mannitol or DCP or MCC) | 15 |
| HPMC | 10 |
| PEO | 20 |
| Colloidal silicon dioxide | 3 |
| Magnesium stearate | 2 |
| IPA | QS |
| Methylene chloride | QS |

Procedure:
i) Sift Rifaximin, diluent and PEO through suitable sieve and mix in a blender.
ii) Add HPMC to IPA: Methylene chloride under stirring.
iii) Granulate (i) with (ii) and dry the wet mass in a fluid bed dryer.
iv) Granules of (iii) passed through suitable sieve.
v) Sift colloidal silicon dioxide and magnesium stearate through specific sieve
vi) Lubricate (iv) with (v).

B) Second Layer

| Ingredients | % w/w |
|---|---|
| HPMC | 50 |
| PEO | 35 |
| Colloidal silicon dioxide | 10 |
| Magnesium stearate | 5 | i) Sift HPMC and PEO through compress both the layers into bilayer tablets. Seive
ii) dry blend (i) in a blender.
iii) sift colloidal silicon dioxide and magnesium stearate through suitable sieve.
iv) Lubricate (ii) with (iii) in a blender.

Compress both A and B to form bilayer tablet or individually compressed into mini-tablets and filled into capsules.

Example 4

| Ingredients | % w/w |
|---|---|
| Rifaximin | 50 |
| Diluents (e.g., Mannitol or DCP or MCC) | 10 |
| HPMC | 10 |
| Sodium Lauryl sulphate | 5 |
| Xanthan gum | 15 |
| Colloidal silicon dioxide | 5 |
| Magnesium stearate | 5 |

Procedure:
i) Sift Rifaximin, Diluent, HPMC, SLS and Xanthan gum through suitable sieve.
ii) Dry blend (i) in a blender.
iii) Sift colloidal silicon dioxide and magnesium stearate through suitable sieve.
iv) Lubricate (ii) with (iii) in a blender.
v) The blend is then compressed into tablets.

Example 5

| Ingredients | % w/w |
|---|---|
| Rifaximin | 50 |
| Diluents (e.g., Mannitol or DCP or MCC) | 15 |
| HPMC | 15 |
| PEO | 15 |
| Colloidal silicon dioxide | 3 |
| Magnesium stearate | 2 |
| Water | QS |

Procedure:
i) Sift Rifaximin, Diluent, HPMC and PEO through suitable sieve.
ii) Dry blend (i) in a blender.
iii) Granulate (ii) with water and dry the wet mass in fluid bed dryer.
iv) Granules obtained in (iii) are sifted through suitable sieve.
v) Sift Colloidal silicon dioxide and magnesium stearate through suitable sieve.
vi) Lubricate (iv) with (v).
vii) Blend of step (vi) is then compressed into tablets.

Example 6

| Ingredients | % w/w |
|---|---|
| Rifaximin | 60 |
| Diluents (e.g., Mannitol or DCP or MCC) | 10 |
| HPMC | 12 |
| PEO | 13 |
| Colloidal silicon dioxide | 3 |
| Magnesium stearate | 2 |
| IPA | QS |
| Methylene chloride | QS |

Procedure:
i) Sift Rifaximin, Diluent, HPMC and PEO through suitable sieve
ii) Dry blend (i) in a blender.
iii) Granulate (ii) with IPA:methylene (70:30) chloride and dry the wet mass in fluid bed dryer.
iv) Granules obtained in (iii) are sifted through suitable sieve.
v) Sift Colloidal silicon dioxide and magnesium stearate through specific sieve.
vi) Lubricate (iv) with (v).
vii) Blend of step (vi) is then compressed into tablets.

Example 7

| Ingredients | % w/w |
|---|---|
| Rifaximin | 50 |
| Diluents (e.g., Mannitol or DCP or MCC) | 15 |
| HPMC | 10 |
| PEO | 15 |
| Colloidal silicon dioxide | 5 |
| Magnesium stearate | 5 |

Procedure:
i) Sift Rifaximin, Diluent, HPMC and PEO through suitable sieve.
ii) Dry blend (i) in a blender.
iii) Sift Colloidal silicon dioxide and magnesium stearate through suitable sieve.
iv) Add half quantity of (iii) to (ii) and mix in a blender.
v) Compact blend of (iv) using a roller compactor at a pressure.
vi) Sift (v) through suitable seive to obtain granules.
vii) Mix remaining quantity of (iii) and (vi) in a blender.
viii) Blend of (vii) is compressed into tablets.

Example 8

A) First and Third Layer

| Ingredients | % W/W |
|---|---|
| HPMC | 40 |
| Xanthan Gum | 20 |
| Carbopol | 25 |
| Collodial Silicon Dioxide | 10 |
| Magnesium Stearate | 5 |

Procedure:
i) Sift HPMC, Xanthan gum and Carbopol through suitable sieve.
ii) Dry blend (i) in a blender.
iii) Sift colloidal silicon dioxide and magnesium stearate through suitable sieve.
iv) Lubricate (ii) with (iii) in a blender.

B) Middle Layer

| Ingredients | % W/W |
|---|---|
| Rifaximin | 40 |
| Diluents (E.g. Mannitol or DCP or MCC) | 30 |
| HPMC | 15 |

-continued

| Ingredients | % W/W |
|---|---|
| Poloxamer | 5 |
| Colloidal silicon dioxide | 5 |
| Magnesium Stearate | 5 | i) Sift Rifaximin, diluent, HPMC, SLS and xanthan gum through suitable sieve ii) Dry blend (i) in a blender.

iii) Sift colloidal silicon dioxide and magnesium stearate through suitable sieve.

iv) Lubricate (ii) with (iii) in a blender.

Blends of A and B are compressed into trilayer tablets

Example 9

A) First and Third Layer

| Ingredients | % W/W |
|---|---|
| HPMC | 40 |
| Xanthan gum | 20 |
| Carbopol | 25 |
| Colloidal silicon dioxide | 10 |
| Magnesium stearate | 5 |

Procedure:

i) Sift HPMC, Xanthan gum and Carbopol through suitable sieve ii) Dry blend (i) in a blender.

iii) Sift colloidal silicon dioxide and magnesium stearate through suitable sieve.

iv) Lubricate (ii) with (iii) in a blender.

B) Middle Layer

| Ingredients | % W/W |
|---|---|
| Rifaximin | 50 |
| Diluents (e.g., Mannitol or DCP or MCC) | 15 |
| HPMC | 10 |
| PEO | 15 |
| Colloidal silicon dioxide | 7 |
| Magnesium stearate | 3 |
| Water | qs | i) Sift Rifaximin, diluent, and PEO through suitable sieve ii) dry blend (i) in a blender.

iii) Mix HPMC in water under stirring iii) Granulate (ii) with (iii) and dry the wet mass in fluid bed dryer.

iv) Granules obtained in (iii) are sifted through suitable sieve.

v) Sift Colloidal silicon dioxide and magnesium stearate through suitable sieve.

vi) Lubricate (iv) with (v).

vii) Blend of A and B is then compressed into trilayered tablet.

Example 10

A) First and Third Layer

| Ingredients | % W/W |
|---|---|
| HPMC | 40 |
| Xanthan gum | 20 |
| Carbopol | 25 |
| Colloidal silicon dioxide | 10 |
| Magnesium stearate | 5 |

Procedure:

i) Sift HPMC, Xanthan gum and Carbopol through suitable sieve.

ii) dry blend (i) in a blender.

iii) sift colloidal silicon dioxide and magnesium stearate through suitable sieve.

iv) Lubricate (ii) with (iii) in a blender.

B) Middle Layer

| Ingredients | % W/W |
|---|---|
| Rifaximin | 40 |
| Diluents (e.g., Mannitol or DCP or MCC) | 20 |
| HPMC | 20 |
| PEO | 15 |
| Colloidal silicon dioxide | 3 |
| Magnesium stearate | 2 |
| IPA | QS |
| Methylene chloride | QS | i) Sift Rifaximin, diluent, and PEO through suitable sieve.

ii) Dry blend (i) in a blender.

iii) Mix HPMC in IPA:Methylene chloride under stirring.

iv) Granulate (ii) with (iii) and dry the wet mass in fluid bed dryer.

v) Granules obtained in (iii) are sifted through suitable sieve.

vi) Sift Colloidal silicon dioxide and magnesium stearate through suitable sieve.

vii) Lubricate (iv) with (v).

Blend A and B are then compressed into trilayer tablet.

Example 11

| Ingredients | % W/W |
|---|---|
| Rifaximin | 30 |
| Xanthan gum | 30 |
| Water | QS |
| Calcium Chloride | 10 |

-continued

| Ingredients | % W/W |
|---|---|
| Water | QS |
| Sodium Alginate | 25 |
| Magnesium Stearate | 5 |

Procedure:
i) Sodium alginate is suspended in water and rifaximin was suspended in this colloidal solution.
ii) Calcium Chloride is dissolved in water and kept aside.
iii) Add step (i) into step (ii) dropwise to make beads under stirring, further filter the solution to separate the beads and dry the beads.
iv) Mix the dried beads with xanthan gum and sodium alginate.
v) Lubricate the beads of step (iv) with magnesium stearate and fill into capsules or sachets or filled in water with sweetening and flavouring agents as a powder for suspension.

Example 12

| Ingredients | % W/W |
|---|---|
| Rifaximin | 40 |
| Diluents (e.g., Mannitol or DCP or MCC) | 30 |
| Sodium CMC | 15 |
| IPA | QS |
| PEO | 10 |
| Magnesium Stearate | 5 |

Procedure:
i) Sift Rifaximin, Diluent, sodium CMC and PEO through suitable sieve.
ii) Granulate blend of step (i) with IPA.
iii) Dry the granules of step (ii) and sift through suitable sieve.
iv) Lubricate the granules of step (iii) with magnesium stearate.
v) The bioadhesive granules of step (iv) can be further compressed into tablets using suitable diluents and lubricants or filled into capsules or sachets or filled into bottle with sweetening and flavouring agents as a powder for suspension.

Example 13

| Ingredients | % W/W |
|---|---|
| Rifaximin | 50 |
| Microcrystalline cellulose (MCC) | 20 |
| PEO | 18 |
| HPMC | 10 |
| IPA | QS |
| Magnesium Stearate | 2 |

Procedure:
Spheronization
i) Sift MCC, Rifaximin, PEO and HPMC through suitable sieve.
ii) Step (i) is mixed with IPA.
iii) Wet mass of step (ii) is passed through Extruder and further spheronized to get the round pellets Hot Melt Extrusion
i) Sift MCC, Rifaximin, PEO and HPMC through suitable sieve.
ii) Step (i) is mixed thoroughly and heated at 70° C.
iii) The soft mass thus obtained is extruded through an extruder and spheronized to get pellets.

The pellets can be filled into capsules, sachets or filled in bottles in water with sweetening and flavouring agents as a powder for suspension or compressed into tablets.

Example 14

| Ingredients | % W/W |
|---|---|
| Rifaximin | 20 |
| Diluents (e.g. Mannitol or DCP or MCC) | 30 |
| Xanthan gum | 15 |
| Poloxamer | 10 |
| Sodium Alginate | 15 |
| Colloidal silicon dioxide | 5 |
| Magnesium Stearate | 5 |

Procedure:
i) Rifaximin, Diluents, Xanthan gum, Poloxamer and sodium alginate are sifted through suitable sieve.
ii) Step (i) is dry blended in a blender.
iii) Lubricants are sifted through specific sieve and mixed with step (ii).
iv) Blend of step (iii) is then compressed into mini tablets.
v) These mini tablets can be filled into capsules.

Example 15

A) First Layer

| Ingredients | % w/w |
|---|---|
| Rifaximin | 90 |
| Hydroxypropylmethyl cellulose HPMC | 5 |
| Colloidal silicon dioxide | 3 |
| Magnesium stearate | 2 |

Procedure:
i) Sift Rifaximin and HPMC through suitable sieve.
ii) Dry blend (i) in a blender.
iii) Sift colloidal silicon dioxide and magnesium stearate through suitable sieve.
iv) Lubricate (ii) with (iii) in a blender.

B) Second Layer

| Ingredients | % w/w |
|---|---|
| HPMC | 49 |
| Polyethylene Oxide (PEO) | 49 |
| Colloidal silicon dioxide | 1 |
| Magnesium stearate | 1 | i) Sift HPMC and PEO through suitable sieve
ii) Dry blend (i) in a blender.
iii) Sift colloidal silicon dioxide and magnesium stearate through suitable sieve.

iv) Lubricate (ii) with (iii) in a blender.

Blends of A and B are then compressed into bilayer tablets or tablet in tablet

Example 16

A) First Layer

| Ingredients | % w/w |
| --- | --- |
| Rifaximin | 50 |
| Diluents (e.g. Mannitol or DCP or MCC) | 15 |
| Hydroxypropylmethyl cellulose HPMC | 15 |
| PEO | 15 |
| Colloidal silicon dioxide | 3 |
| Magnesium stearate | 2 |
| Water | QS |

Procedure:
i) Sift Rifaximin, diluent and PEO through specific sieve and mix in a blender.
ii) Add HPMC to water under stirring.
iii) Granulate (i) with (ii) and dry the wet mass in a fluid bed dryer.
iv) Granules of (iii) passed through suitable sieve.
v) Sift colloidal silicon dioxide and magnesium stearate through suitable sieve.
vi) Lubricate (iv) with (v).

B) Second Layer

| Ingredients | % w/w |
| --- | --- |
| HPMC | 81.5 |
| PEO | 16 |
| Colloidal silicon dioxide | 1.5 |
| Magnesium stearate | 1 | i) Sift HPMC and PEO through suitable sieve
ii) Dry blend (i) in a blender.
iii) Sift colloidal silicon dioxide and magnesium stearate through suitable sieve.
iv) Lubricate (ii) with (iii) in a blender.

Compress both A and B to form bilayer tablet.

Example 17

A) First Layer

| Ingredients | % w/w |
| --- | --- |
| Rifaximin | 50 |
| Diluents (e.g. Mannitol or DCP or MCC) | 15 |
| Hydroxypropylmethyl cellulose HPMC | 10 |
| PEO | 20 |
| Colloidal silicon dioxide | 3 |
| Magnesium stearate | 2 |
| IPA | QS |
| Methylene Chloride | QS |

Procedure:
i) Sift Rifaximin, diluent and PEO through suitable sieve and mix in a blender.
ii) Add HPMC to IPA:Methylene chloride under stirring.
iii) Granulate (i) with (ii) and dry the wet mass in a fluid bed dryer.
iv) Granules of (iii) passed through suitable sieve.
v) Sift colloidal silicon dioxide and magnesium stearate through specific sieve
vi) Lubricate (iv) with (v).

B) Second Layer

| Ingredients | % w/w |
| --- | --- |
| HPMC | 49 |
| PEO | 49 |
| Colloidal silicon dioxide | 1 |
| Magnesium stearate | 1 | i) Sift HPMC and PEO through suitable sieve
ii) Dry blend (i) in a blender.
iii) Sift colloidal silicon dioxide and magnesium stearate through suitable sieve.
iv) Lubricate (ii) with (iii) in a blender.

Compress both A and B to form bilayer tablet.

Example 18

| Ingredients | % w/w |
| --- | --- |
| Rifaximin | 40 |
| Diluents (e.g., Mannitol or DCP or MCC | 17 |
| HPMC | 20 |
| Sodium Lauryl sulphate | 5 |
| Xanthan gum | 15 |
| Colloidal silicon dioxide | 2 |
| Magnesium stearate | 1 |

Procedure:
i) Sift Rifaximin, Diluent, HPMC, SLS and Xanthan gum through suitable sieve.
ii) Dry blend (i) in a blender.
iii) Sift colloidal silicon dioxide and magnesium stearate through suitable sieve.
iv) Lubricate (ii) with (iii) in a blender.
v) The blend is then compressed into tablets.

HPMC=Hydroxy propyl methyl cellulose
PEO=Polyethyeleneoxide
DCP=Dicalcium phosphate
MCC=Microcrystalline cellulose
MA 1=Methacrylic acid copolymer L 100
MA2=Methacrylic acid copolymer S 100
IPA=Isopropyl Alcohol Dissolution The formulations of the invention have a prolonged in vitro release rate. The in vitro test used to measure release rate of the active agent from a formulation of the invention was as follows. A solution of 900 ml of a 6.8 pH phosphate buffer, 1.5% SLS was placed in an apparatus capable of agitation. The apparatus used in present invention is type II Paddle dissolution apparatus, and rotated at a speed of 100 rpm. The tablet formulation was placed in the apparatus and dissolution was periodically measured. The in vitro dissolution studies of Example 1 is such that about 20% to 50% of drug is released in about 8 hrs, about 30% to about 70% of drug is released in about 12 hrs and about more than 70% of drug is released in about 24 hrs.

Determination of Bioadhesion

Figure 1:
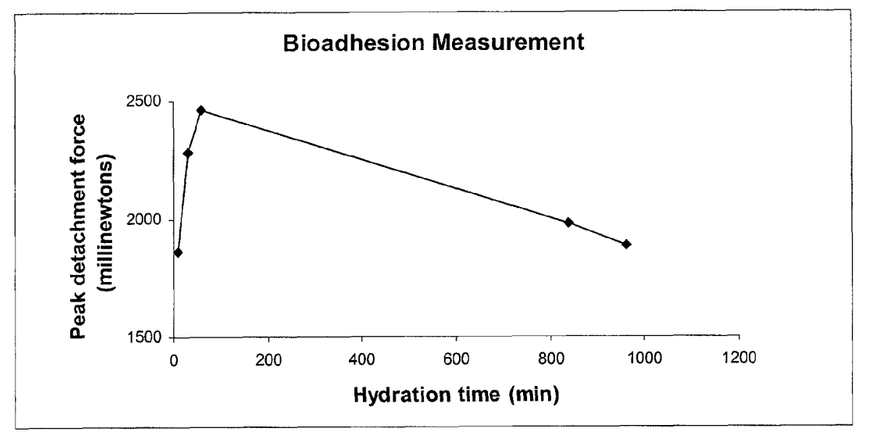
FIG. 1 is a graph showing the Bioadhesion Measurement with peak detachment force as a function of hydration time. As determined by tensionmetric method, the force required to separate the tablet from biological substrate was recorded in mN. Support for this is found on page 33 in the Determination of Bioadhesion section of the specification.

Bioadhesion was determined by tensiometric method. For the determination, an advanced force gauge equipment (mfg. by Mecmesin, West Sussex, England) was used. Freshly excised Sheep intestinal tissue was taken and stored in a Tyrode solution at 4° C. until used for the experiment. The tissue was cut into pieces (3×4 cm) and mounted on the glass slide and tightened with a thread. 0.5 ml Phosphate buffered saline (PBS) was placed on the tissue. The bioadhesive tablet of the present invention was placed on this tissue and another 0.5 ml PBS was placed on the tablet. A glass slide with a 10 g weight was placed on the tablet and it was allowed to hydrate for 10 min., 30 min., 60 min., and 840 min. At the specific time interval, the hydrated tablet along with slide was mounted on the stage of the bioadhesion apparatus. Probe was then lowered at fixed speed of 0.2 mm/sec. and upper slide was attached to the hook of the probe by means of a thread. The peak detachment force was considered as the bioadhesive force as evident from the graph as provided in FIG. 1. The force required to separate the tablet from biological substrate was recorded in mN.

Treatment of Traveler's Diarrhea

A randomized, open labeled, multi-centered, comparative pilot clinical trial was carried out using the medicinal preparation containing extended release tablet containing 600 mg of rifaximin, administered once daily as test and commercially marketed dosage form containing 200 mg of rifaximin given thrice daily (Xifaxan®) as reference. The study was designed to demonstrate the similar clinical efficacy compared to Xifaxan®.

*E. Coli* is the baseline pathogen with sufficient numbers to determine the similar clinical efficacy compared to Xifaxan®.

The primary efficacy endpoint was time to last unformed stool (TLUS) and secondary end point was eradication of pathogen. Therapy was taken for 3 days. The intent to treat (ITT) population was defined as all subjects randomized to treatment.

A total of 66 patients were randomized to receive study treatment. Out of this 33 were randomized to receive rifaximin ER and 31 to receive Xifaxan®. In rifaximin group 20 out of 33 patients were *E. coli* positive. In Xifaxan® group 14 out of 31 were *E. coli* positive. The results of TLUS are presented in Table 1, Table 2 and Table 3 for the ITT, *E. coli* positive patients and *E. Coli* eradication respectively. TLUS was measured in hours.

TABLE 1

Mean TLUS For ITT Population

|  | Rifaxmin ER 600 mg OD Mean (hrs) | Xifaxan ® 200 mg TID Mean (hrs) |
|---|---|---|
| Site 1 | 58.81 (n = 19) | 60.56 (n = 19) |
| Site 2 | 34.90 (n = 14) | 34.35 (n = 12) |

Time for last unformed stools for intent to treat population ranges from about 8 to about 90 hrs, preferably from about 10 to about 85 hrs.

TABLE 2

Mean TLUS For *E. Coli* Positive Population

|  | Rifaxmin ER 600 mg OD Mean (hrs) | Xifaxan ® 200 mg TID Mean (hrs) |
|---|---|---|
| Site 1 | 60.52 (n = 14) | 60.52 (n = 6) |
| Site 2 | 44.16 (n = 6) | 37.54 (n = 8) |

Time for last unformed stools for *E. coli* positive population ranges from about 20 to about 90 hrs, preferably from about 25 to about 85 hrs.

TABLE 3

Microbiological Eradication Post Treatment

|  | Rifaximin ER 600 mg OD | Xifaxan ® 200 mg TID |
|---|---|---|
| Site 1 | 100% (n = 14) | 100% (n = 6) |
| Site 2 | 83.33*% (n = 6) | 100% (n = 8) |

*At the end of treatment one patient was still *E. Coli* positive.

Based on the above results, it can be stated that rifaximin ER will increases patient compliance as it is similar in efficacy to Xifaxan® but has to be administered once daily in comparison to Xifaxan® which is administered thrice daily.

Further, it has been surprisingly found that rifaximin ER 600 mg given once daily was also effective in treating *Klebsiella* caused traveler's diarrhea.

The invention claimed is:

1. A controlled release pharmaceutical composition comprising:
   a. a single active agent consisting of a therapeutically effective amount of rifaximin or pharmaceutically acceptable salt(s) or enantiomer(s) or polymorph(s) thereof;
   b. one or more release controlling agent(s); and
   c. pharmaceutically acceptable excipient(s);
   wherein the pharmaceutical composition has an in vitro dissolution profile, when measured in a type II Paddle dissolution apparatus, in 6.8 phosphate buffer with 1.5% SLS at about 100 rpm, in which about 20% to about 50% of the drug is released in about 8 hrs, about 30% to about 70% of drug is released in about 12 hrs and about more than 70% of drug is released in about 24 hrs.

2. The controlled release pharmaceutical composition according to claim 1, wherein the composition is formulated to increase the residence time of rifaximin in the gastrointestinal tract.

3. The controlled release pharmaceutical composition according to claim 2, wherein the increase in residence time of rifaximin formulation in the gastrointestinal tract is achieved by bioadhesion using one or more bioadhesive polymer(s).

4. The controlled release pharmaceutical composition according to claim 3, wherein the polymer comprises polycarbophils, carbomers, lectins, pectin, zein, modified zein, casein, gelatin, gluten, serum albumin, collagen, chitosan, cellulose, methyl cellulose, ethyl cellulose, hydroxypropyl cellulose, hydroxypropylmethyl cellulose, hydroxybutylmethyl cellulose, cellulose acetate, cellulose propionate, cellulose acetate butyrate, cellulose acetate phthalate, carboxymethyl cellulose, cellulose triacetate, cellulose sulfate sodium salt, dextrans, tamarind seed polysaccharide, gellan, carrageenan; hyaluronic acid, polyhyaluronic acid, alginic acid, sodium alginate; gum; polyvinylacetate, polyvinylalcohol, povidone/polyethylene oxide, acrylic and methacrylic acid their copolymers, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, polystyrene, polymers of acrylic and methacrylic esters, polylactides, poly (butyric acid), poly(valeric acid), poly(lactide-co-glycolide), polyanhydrides, polyorthoesters, poly(fumaric acid), poly (maleic acid), polymers having a hydrophobic backbone with at least one hydrophilic group pendant from the backbone, polymers having a hydrophobic backbone with at least one hydrophobic group pendant from the backbone, blends thereof, copolymers thereof; or mixtures thereof.

5. The controlled release pharmaceutical composition according to claim 1, wherein the release controlling agent comprises hydrophilic polymer, hydrophobic agent, or mixtures thereof.

6. The controlled release pharmaceutical composition according to claim 5, wherein the hydrophilic polymer comprises cellulose, ethylcellulose, hydroxypropylcellulose, hydroxypropylmethylcellulose, hydroxypropylethylcellulose; xanthan gum, guar gum, locust bean gum; alginates; carbomer; polyvinylacetate, polyvinylalcohol, povidone/polyethylene oxide, acrylic and methacrylic acid copolymers, or mixtures thereof.

7. The controlled release pharmaceutical composition according to claim 5, wherein the hydrophobic release component comprises beeswax; fatty acids; long chain fatty alcohols, such as cetyl alcohol, myristyl alcohol, stearyl alcohol; glycerides such as glyceryl esters of fatty acids like glyceryl monostearate, glyceryl distearate, glyceryl esters of hydrogenated castor oil, mineral oil, hydrogenated vegetable oil, acetylated glycerides; ethyl cellulose, stearic acid, paraffin, carnauba wax, talc; stearate salts such as calcium, magnesium, zinc or mixtures thereof.

8. The controlled release pharmaceutical composition according to claim 1, further comprising a solubilizing agent comprising surfactant; cyclodextrin and its derivatives; lipophilic substances; vitamin E and its derivatives; monohydric alcohol esters; nitrogen-containing solvents; phospholipids; glycerol acetates; glycerol fatty acid esters; propylene glycol esters; ethylene glycol esters; or a mixture thereof.

9. The controlled release pharmaceutical composition according to claim 1, wherein the pharmaceutically acceptable excipient comprises binders, diluents, lubricants, surfactants, glidants, or mixtures thereof.

10. The controlled release pharmaceutical composition according to claim 9, wherein the binder comprises cellulose, cellulose derivative; starches; gums; polyvinylpyrrolidone, povidone, syrup, polyethylene oxide, polyacryl amide, poly-N-vinyl amide, sodium carboxymethyl cellulose, polyethylene glycol, gelatin, polyethylene oxide, poly propylene glycol, tragacanth, alginic acid, or mixtures thereof.

11. The controlled release pharmaceutical composition according to claim 9, wherein the diluent comprises carbohydrates, derivatives of carbohydrates, polyols, sugar alcohols, carbonate, sulphate or phosphate salts of inorganic metals, or mixtures thereof.

12. The controlled release pharmaceutical composition according to claim 9, wherein the lubricant comprises magnesium, aluminium, zinc or calcium stearate, sodium stearyl fumarate, polyethylene glycol, mineral oil, stearic acid, hydrogenated vegetable oil, glyceryl behenate, glyceryl palmitostearate, glyceryl stearate, cornstarch, talc, calcium silicate, magnesium silicate, colloidal silicon dioxide, silicon hydrogel, or mixtures thereof.

13. The controlled release pharmaceutical composition according to claim 9, wherein the surfactant comprises ionic or non-ionic or zwitterionic surfactants.

14. The controlled release pharmaceutical composition according to claim 9, wherein the glidant comprises silicon dioxide, colloidal silica, powdered cellulose, talc, tribasic calcium phosphate, or mixtures thereof.

15. The controlled release pharmaceutical composition according to claim 1, which is a once-daily dosage form.

16. The controlled release pharmaceutical composition according to claim 1, which is a once-daily dosage form comprising 20 to 2400 mg of rifaximin.

17. The controlled release pharmaceutical composition according to claim 1, which is a once-daily dosage form comprising 550 mg of rifaximin.

18. The controlled release pharmaceutical composition according to claim 1, which is a once-daily dosage form comprising 600 mg of rifaximin.

19. A method comprising, administering a controlled release pharmaceutical composition according to claim 1 to increase patient compliance for treatment of traveler's diarrhea, hepatic encephalopathy, infectious diarrhea, diverticular disease, an antibacterial prophylactic prior to colon surgery, irritable bowel syndrome, Crohn's disease, *Clostridum difficile*-associated diarrhea, small intestinal bacterial overgrowth, traveler's diarrhea prophylaxis, dysentery, pouchitis, peptic ulcer disease, surgical prophylaxis, or gastric dyspepsia.

20. A method comprising, administering a controlled release pharmaceutical composition according to claim 1 to treat traveler's diarrhea, hepatic encephalopathy, infectious diarrhea, diverticular disease, an antibacterial prophylactic prior to colon surgery, irritable bowel syndrome, Crohn's disease, *Clostridum difficile*-associated diarrhea, small intestinal bacterial overgrowth, traveler's diarrhea prophylaxis, dysentery, pouchitis, peptic ulcer disease, surgical prophylaxis, or gastric dyspepsia.

21. The method of claim 20, comprising administering the controlled release pharmaceutical composition according to claim 1 for the treatment of traveler's diarrhea.

22. The method of claim 21, comprising administering the controlled release pharmaceutical composition according to claim 1 for the treatment of traveler's diarrhea caused by *E. coli*.

23. A method of treating *klebsiella* induced traveler's diarrhea comprising administering a once daily controlled release pharmaceutical composition comprising:
   a. a single active agent consisting of therapeutically effective amount of rifaximin or pharmaceutically acceptable salt(s) or enantiomer(s) or polymorph(s) thereof;
   b. one or more release controlling agent(s); and
   c. pharmaceutically acceptable excipient(s);
wherein the pharmaceutical composition has an in vitro dissolution profile, when measured in a type II Paddle dissolution apparatus, in 6.8 phosphate buffer with 1.5% SLS at about 100 rpm, in which about 20% to about 50% of the drug is released in about 8 hrs, about 30% to about 70% of drug is released in about 12 hrs and about more than 70% of drug is released in about 24 hrs.

24. The controlled release pharmaceutical composition according to claim 1, comprising a coating, wherein the coating comprises film coating, sugar coating, enteric coating, bioadhesive, or mucoadhesive coating.

25. The controlled release pharmaceutical composition according to claim 24, wherein the coating comprises coating agents, plasticizers, antitacking agents, surfactants, coloring agents, opacifiers, or mixtures thereof.

26. A controlled release pharmaceutical composition of rifaximin according to claim 1 comprising: at least two entities wherein one entity is an immediate release or fast release and the other is controlled release.

27. The controlled release pharmaceutical composition of rifaximin according to claim 1, comprising: at least two entities wherein one entity is controlled release and the other is bioadhesive.

28. The controlled release pharmaceutical composition according to claim 1, which is in the form of tablets, pellets, beads, granules, sustained release formulations, capsules, microcapsules, tablets in capsules, microspheres or powders/pellets/beads/granules for suspension.

29. The controlled release pharmaceutical composition according to claim 28 wherein the tablets comprise single layered tablets, multilayered tablets, mini tablets, bioadhesive tablets, caplets, matrix tablets, tablet within a tablet, mucoadhesive tablets, modified release tablets, pulsatile release tablets, and timed release tablets.

30. A controlled release pharmaceutical composition in the form of a multilayer tablet according to claim 1 comprising, a) at least one layer which comprises, a therapeutically effective amount of rifaximin or a pharmaceutically acceptable salt(s) or enantiomer(s) or polymorph(s) thereof, pharmaceutically acceptable excipient(s); wherein the said layer provides a controlled release rifaximin; and b) at least one layer which provides increased residence time of the dosage form in the gastrointestinal tract.

31. A controlled release pharmaceutical composition comprising:
   a. a single active agent consisting of a therapeutically effective amount of rifaximin or a pharmaceutically acceptable salt(s) or enantiomer(s) or polymorph(s) thereof;
   b. one or more release controlling agent(s); and
   c. pharmaceutically acceptable excipient(s);
wherein the composition is formulated to increase the residence time of rifaximin in the gastrointestinal tract having an adhesive strength, measured as a force of detachment, of at least 100 mN when measured using advanced force gauge equipment;
wherein the pharmaceutical composition has an in vitro dissolution profile, when measured in a type II Paddle dissolution apparatus, in 6.8 phosphate buffer with 1.5% SLS at about 100 rpm, in which about 20% to about 50% of the drug is released in about 8 hrs, about 30% to about 70% of drug is released in about 12 hrs and about more than 70% of drug is released in about 24 hrs.

32. A once daily controlled release pharmaceutical composition comprising:
   a. a single active agent consisting of therapeutically effective amount of rifaximin or pharmaceutically acceptable salt(s) or enantiomer(s) or polymorph(s) thereof;
   b. one or more release controlling agent(s); and
   c. pharmaceutically acceptable excipient(s);
which results in eradication of at least 70% of pathogens;
wherein the pharmaceutical composition has an in vitro dissolution profile, when measured in a type II Paddle dissolution apparatus, in 6.8 phosphate buffer with 1.5% SLS at about 100 rpm, in which about 20% to about 50% of the drug is released in about 8 hrs, about 30% to about 70% of drug is released in about 12 hrs and about more than 70% of drug is released in about 24 hrs.

33. The once daily controlled release pharmaceutical composition according to claim 32, wherein the pathogen is *E. coli*.

34. The once daily controlled release pharmaceutical composition according to claim 32, wherein the pathogen is *Klebsiella*.

35. A once daily controlled release pharmaceutical composition comprising:
   a. a single active agent consisting of therapeutically effective amount of rifaximin or pharmaceutically acceptable salt(s) or enantiomer(s) or polymorph(s) thereof;
   b. one or more release controlling agent(s); and
   c. pharmaceutically acceptable excipient(s);
   wherein the pharmaceutical composition results in time for last unformed stools for intent to treat population in the range of about 8 to about 90 hrs;
wherein the pharmaceutical composition has an in vitro dissolution profile, when measured in a type II Paddle dissolution apparatus, in 6.8 phosphate buffer with 1.5% SLS at about 100 rpm, in which about 20% to about 50% of the drug is released in about 8 hrs, about 30% to about 70% of drug is released in about 12 hrs and about more than 70% of drug is released in about 24 hrs.

36. The once daily controlled release pharmaceutical composition according to claim 35, wherein the pharmaceutical composition results in time for last unformed stools for intent to treat population in the range of about 10 to about 85 hrs.

37. The once daily controlled release pharmaceutical composition according to claim 35, wherein the pharmaceutical composition results in time for last unformed stools for *E. coli* positive population in the range of about 20 to about 90 hrs.

38. The once daily controlled release pharmaceutical composition according to claim 37, wherein the pharmaceutical composition results in time for last unformed stools for *E. coli* positive population in the range of about 25 to about 85 hrs.

39. The controlled release pharmaceutical composition of claim 1, wherein the active agent comprises an antibiotic and the antibiotic is a therapeutically effective amount of rifaximin or pharmaceutically acceptable salt(s) or enantiomer(s) or polymorph(s) thereof.

* * * * *